United States Patent
Park et al.

(10) Patent No.: US 7,816,667 B2
(45) Date of Patent: *Oct. 19, 2010

(54) SILSESQUIOXANE-BASED COMPOUND AND ORGANIC LIGHT-EMITTING DEVICE INCLUDING THE SAME

(75) Inventors: Jong-Jin Park, Yongin-si (KR); Tae-Woo Lee, Seoul (KR); Masa-Aki Kakimoto, Tokyo (JP); Lyong-Sun Pu, Suwon-si (KR)

(73) Assignee: Samsung Mobile Display Co., Ltd., Nongseo-Dong, Giheung-Gu, Yongin-City, Gyunggi-Do (KR)

( * ) Notice: Subject to any disclaimer, the term of this patent is extended or adjusted under 35 U.S.C. 154(b) by 810 days.

This patent is subject to a terminal disclaimer.

(21) Appl. No.: 11/509,621

(22) Filed: Aug. 25, 2006

(65) Prior Publication Data

US 2007/0045619 A1 Mar. 1, 2007

(30) Foreign Application Priority Data

Aug. 25, 2005 (KR) ............ 10-2005-0078426

(51) Int. Cl.
*H01L 51/54* (2006.01)
*C08G 77/04* (2006.01)

(52) U.S. Cl. ............ 257/40; 257/E51.046; 528/10; 528/32; 528/37; 313/504; 428/690

(58) Field of Classification Search ............ 257/40, 257/E51.026, E51.046; 438/99; 528/10, 528/31–33, 35–37, 40, 43; 313/504; 428/690; 252/62.3 Q, 301.16–301.35
See application file for complete search history.

(56) References Cited

U.S. PATENT DOCUMENTS 6,517,958 B1 * 2/2003 Sellinger et al. ............ 428/690
6,830,830 B2 * 12/2004 Hsieh et al. ............ 428/690
2003/0120099 A1 * 6/2003 Laine et al. ............ 556/450

(Continued)

FOREIGN PATENT DOCUMENTS

DE    10304735 A1 *  7/2004

(Continued)

OTHER PUBLICATIONS

Lin, W.-J., et al. "Synthesis and Optoelectronic Properties of Starlike Polyflourenes with a Silsesquioxane Core." Macromolecules, vol. 37 (2004): pp. 2335-2341.*

(Continued)

*Primary Examiner*—Matthew W Such
(74) *Attorney, Agent, or Firm*—Robert E. Bushnell, Esq.

(57) ABSTRACT

A silsesquioxane-based compound represented by Formula 1 and an organic light-emitting device including the same:

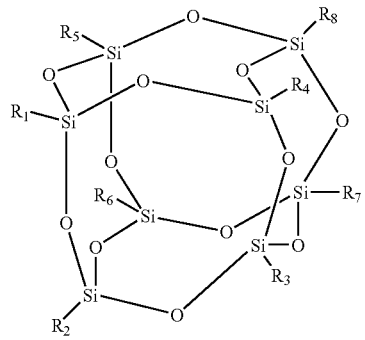

<Formula 1> wherein $R_1$, $R_2$, $R_3$, $R_4$, $R_5$, $R_6$, $R_7$, and $R_8$ are as defined in the specification. The use of the silsesquioxane-based compound enables to produce an organic light-emitting device with improvement in electrical characteristics such as brightness and efficiency. The silsesquioxane-based compound can exhibit good film smoothness and adhesion, and at the same time, good electrical characteristics such as current efficiency and brightness, and thus, is suitable for use in an organic light-emitting device.

19 Claims, 3 Drawing Sheets

U.S. PATENT DOCUMENTS

| | | | |
|---|---|---|---|
| 2003/0204038 A1* | 10/2003 | Xiao et al. | 528/10 |
| 2004/0024164 A1* | 2/2004 | Lyu et al. | 528/10 |
| 2005/0035346 A1* | 2/2005 | Bazan et al. | 257/40 |
| 2005/0123760 A1* | 6/2005 | Cammack et al. | 428/403 |
| 2007/0138483 A1* | 6/2007 | Lee et al. | 257/79 |

FOREIGN PATENT DOCUMENTS

| | | | |
|---|---|---|---|
| JP | 2006108458 A * | 4/2006 | |
| KR | 1020040070561 | 8/2004 | |

OTHER PUBLICATIONS

Brick, C.M., et al. "Robust Polyaromatic Octasilsesquioxanes from Polybromophenylsilsesquioxanes, BrxOPS, via Suzuki Coupling." Macromolecules, vol. 38 (2005): pp. 4661-4665.*

Machine Translation of JP 2006108458.*

He, C., et al. "Highly Efficient Luninescent Organic Clusters with Quantum Dot-Like Properties." J. Am. Chem. Soc., vol. 126 (2004): pp. 7792-7793.*

Hoebbel, D., et al. "Synthesis and Properties of Perfluoroalkyl Groups Containing Double Four-Ring Spherosilicate (Siloxysilsesquioxane) Precursors." J. Sol-Gel Sci. Tech., vol. 24 (2002): pp. 121-129.*

* cited by examiner

SILSESQUIOXANE-BASED COMPOUND AND ORGANIC LIGHT-EMITTING DEVICE INCLUDING THE SAME

CROSS-REFERENCE TO RELATED PATENT APPLICATION AND CLAIM OF PRIORITY

This application claims priority from Korean Patent Application No. 10-2005-0078426, filed on Aug. 25, 2005, in the Korean Intellectual Property Office, the disclosure of which is incorporated herein in its entirety by reference.

1. FIELD OF THE INVENTION

The present invention relates to a silsesquioxane-based compound and an organic light-emitting device including the same. More particularly, the present invention relates to a silsesquioxane-based compound achieving good efficiency and brightness when applied to an organic light-emitting device, and an organic light-emitting device including the same.

2. DESCRIPTION OF THE RELATED ART

Light-emitting devices are self-emitting devices and have advantages such as a wide viewing angle, good contrast, and a rapid response time. Light-emitting devices are classified into inorganic light-emitting devices using a light-emitting layer made of an inorganic compound and Organic Light-Emitting Devices (OLEDs) using a light-emitting layer made of an organic compound. OLEDs show better brightness, driving voltage, and response speed characteristics and can achieve polychromatic changes, compared to inorganic light-emitting devices, and thus there have been many researches about OLEDs.

Generally, OLEDs have a stacked structure of an anode, an organic light-emitting layer, and a cathode. OLEDs may also have various structures such as anode/hole injection layer/hole transport layer/light-emitting layer/electron transport layer/electron injection layer/cathode or anode/hole injection layer/hole transport layer/light-emitting layer/hole blocking layer/electron transport layer/electron injection layer/cathode. An example of OLEDs is disclosed in Korean Patent Laid-Open Publication No. 2004-0070561.

However, conventional OLEDs have unsatisfactory electrical characteristics, and thus, there is room for improvement in the conventional OLEDs.

SUMMARY OF THE INVENTION

The present invention provides a silsesquioxane-based compound capable of effectively controlling hole or electron transport, and an organic light-emitting device with improved electrical characteristics including the silsesquioxane-based compound.

According to an aspect of the present invention, there is provided a silsesquioxane-based compound represented by Formula 1 below:

<Formula 1> wherein $R_1$, $R_2$, $R_3$, $R_4$, $R_5$, $R_6$, $R_7$, and $R_8$ are each independently a substituent having a hole transport moiety, a substituent having an electron transport moiety, or a substituent having a cross-linkable moiety, and at least one of $R_1$, $R_2$, $R_3$, $R_4$, $R_5$, $R_6$, $R_7$, and $R_8$ is a substituent having a cross-linkable moiety.

According to another aspect of the present invention, there is provided an organic light-emitting device including: a first electrode; a second electrode; a light-emitting layer interposed between the first electrode and the second electrode; and a carrier transport layer, interposed between the first electrode and the second electrode, including the above-described silsesquioxane-based compound.

The carrier transport layer including the silsesquioxane-based compound can effectively control hole or electron transport, and achieve good film smoothness. Therefore, the organic light-emitting device including the carrier transport layer can have good electrical characteristics.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Embodiments of the present invention will now be described more fully with reference to the accompanying drawings, in which exemplary embodiments of the invention are shown.

The present invention provides a silsesquioxane-based compound represented by Formula 1 below:

<Formula 1>

The silsesquioxane-based compound of Formula 1 has two heterocyclic rings having Si—O—Si bonds. The two heterocyclic rings are joined by connecting a Si atom of one heterocyclic ring to a Si atom of the other heterocyclic ring via an oxygen (O) atom.

$R_1$, $R_2$, $R_3$, $R_4$, $R_5$, $R_6$, $R_7$, and $R_8$ bound to the Si atoms in the silsesquioxane-based compound of Formula 1 are each independently a substituent having a hole transport moiety, a substituent having an electron transport moiety, or a substitu- ent having a cross-linkable moiety. At this time, at least one of $R_1$, $R_2$, $R_3$, $R_4$, $R_5$, $R_6$, $R_7$, and $R_8$ is a substituent having a cross-linkable moiety. If none of $R_1$, $R_2$, $R_3$, $R_4$, $R_5$, $R_6$, $R_7$, and $R_8$ are a substituent having a cross-linkable moiety, crosslinking does not occur, thereby lowering the characteristics (e.g., durability, surface morphology, or adhesion) of a film including the silsesquioxane-based compound.

According to an embodiment of the silsesquioxane-based compound, $R_1$, $R_2$, $R_3$, $R_4$, $R_5$, $R_6$, $R_7$, and $R_8$ may be each independently a substituent having a hole transport moiety or a substituent having a cross-linkable moiety.

According to another embodiment of the silsesquioxane-based compound, $R_1$, $R_2$, $R_3$, $R_4$, $R_5$, $R_6$, $R_7$, and $R_8$ may be each independently a substituent having an electron transport moiety or a substituent having a cross-linkable moiety.

The silsesquioxane-based compound of an embodiment of the present invention may be represented by Formula 2 below:

port. Examples of the hole transport moiety include, but are not limited to,

<Formula 2>

$R_1$, $R_2$, $R_3$, $R_4$, $R_5$, $R_6$, $R_7$, and $R_8$ of Formula 1 are more specifically described in Formula 2.

In Formula 2, a, b, c, d, e, f, g, and h may be each independently an integer of 1 to 20. Each of a, b, c, d, e, f, g, and h corresponds to the number of carbons in an alkylene spacer connecting each Si of the silsesquioxane-based compound to $T_1$, $T_2$, $T_3$, $T_4$, $T_5$, $T_6$, $T_7$, or $T_8$. The alkylene spacer serves to enhance the solubility of the silsesquioxane-based compound in a solvent and film uniformity.

In particular, if the number of carbons in the alkylene spacer exceeds 20, the substituents (i.e., $R_1$, $R_2$, $R_3$, $R_4$, $R_5$, $R_6$, $R_7$, and $R_8$) binding with the Si atoms of the silsesquioxane-based compound may become overflexible, thereby lowering the density of film formation compounds after curing. Thus, the number of carbons in the alkylene spacer may be 20 or less.

Preferably, each of a, b, c, d, e, f, g, and h may be 1 to 15.

$T_1$, $T_2$, $T_3$, $T_4$, $T_5$, $T_6$, $T_7$, and $T_8$ may be each independently C or Si. $X_1$, $X_2$, $X_3$, $X_4$, $X_5$, $X_6$, $X_7$, $X_8$, $Y_1$, $Y_2$, $Y_3$, $Y_4$, $Y_5$, $Y_6$, $Y_7$, and $Y_8$ may be each independently hydrogen or an $C_1$-$C_{20}$ alkyl group, preferably a $C_1$-$C_{15}$ alkyl group, and $Z_1$, $Z_2$, $Z_3$, $Z_4$, $Z_5$, $Z_6$, $Z_7$, and $Z_8$ may be each independently a hole transport moiety, an electron transport moiety, or a cross-linkable moiety. At least one of $Z_1$, $Z_2$, $Z_3$, $Z_4$, $Z_5$, $Z_6$, $Z_7$, and $Z_8$ is a cross-linkable moiety.

The hole transport moiety which can be included in the silsesquioxane-based compound of an embodiment of the present invention serves to effectively facilitate hole trans- -continued , and  where $O_1$,

$Q_2$, $Q_3$, $Q_4$, $Q_5$ may be each independently N, O, or S.

The hole transport moiety may be substituted by various substituents. For example, the hole transport moiety may be substituted by at least one of a hydroxyl group, an amino group, a halogen atom, a cyano group, a $C_1$-$C_{20}$ alkyl group, and a $C_1$-$C_{20}$ alkoxy group, but the present invention is not limited thereto.

More specifically, the substituent having the hole transport moiety may be represented by Formula 3 below, but is not limited thereto:

The electron transport moiety included in the silsesquioxane-based compound of an embodiment of the present invention serves to effectively facilitate electron transport. Examples of the electron transport moiety include, but are not limited to, where $Q_6$, $Q_7$, and $Q_8$ are each independently N, O, or S.

The electron transport moiety may be substituted by various substituents. For example, the electron transport moiety may be substituted by at least one of a hydroxyl group, an amino group, a halogen atom, a cyano group, a $C_1$-$C_{20}$ alkyl group, and a $C_1$-$C_{20}$ alkoxy group, but is not limited thereto.

More specifically, the substituent having the electron transport moiety may be represented by Formula 4 below, but is not limited thereto:

<Formula 4>

The cross-linkable moiety included in the silsesquioxane-based compound of an embodiment of the present invention is a moiety enabling a cross-linkage between silsesquioxane-based compounds, and serves to increase the thermal stability and adhesion of a film including a silsesquioxane-based compound.

More specifically, the cross-linkable moiety may be represented by —Si($M_1$)($M_2$)($M_3$) where $M_1$, $M_2$, and $M_3$ are each independently hydrogen, a $C_1$-$C_{20}$ alkyl group, a $C_1$-$C_{20}$ alkoxy group, or a halogen group, and at least one of $M_1$, $M_2$, and $M_3$ is a $C_1$-$C_{20}$ alkoxy group or a halogen group. The $C_1$-$C_{20}$ alkoxy group and the halogen group are cross-linkable groups.

The silsesquioxane-based compound of an embodiment of the present invention may include a substituent having a cross-linkable moiety as represented by Formula 5 below, but the present invention is not limited thereto:

<Formula 5>

According to an embodiment of the present invention, the silsesquioxane-based compound may be represented by Formula 6 or 7 below, but is not limited thereto:

<Formula 6>

<Formula 7>

-continued

The silsesquioxane-based compound of Formula 1 can be synthesized by a common organic synthesis principle, which is obvious to those of ordinary skilled in the art.

The above-described silsesquioxane-based compound of an embodiment of the present invention can be applied to an organic light-emitting device. Thus, an embodiment of the present invention provides an organic light-emitting device including: a first electrode; a second electrode; a light-emitting layer interposed between the first electrode and the second electrode; and a carrier transport layer, interposed between the first electrode and the second electrode, including the above-described silsesquioxane-based compound.

The carrier transport layer including the silsesquioxane-based compound of an embodiment of the present invention is interposed between the first electrode and the second electrode, more specifically, between the first electrode and the light-emitting layer or between the light-emitting layer and the second electrode.

For example, in a case where the silsesquioxane-based compound includes a substituent having a hole transport moiety and a substituent having a cross-linkable moiety, the carrier transport layer may be interposed between the first electrode and the light-emitting layer. On the other hand, in a case where the silsesquioxane-based compound includes a substituent having an electron transport moiety and a substituent having a cross-linkable moiety, the carrier transport layer may be interposed between the light-emitting layer and the second electrode.

The carrier transport layer including the silsesquioxane-based compound may further include metal nanoparticles. The metal nanoparticles serve to enhance hole transport capability of a hole transport moiety and/or electron transport capability of an electron transport moiety.

The metal nanoparticles may be preferably at least one of Au, Ag, Cu, Pd, and Pt nanoparticles.

The metal nanoparticles may have an average particle size of 5 to 20 nm. If the average particle size of the metal nanoparticles is less than 5 nm, the nanoparticles may be easily conglomerated. On the other hand, if the average particle size of the metal nanoparticles exceeds 20 nm, it may be difficult to adjust a surface smoothness.

Figure 1A:
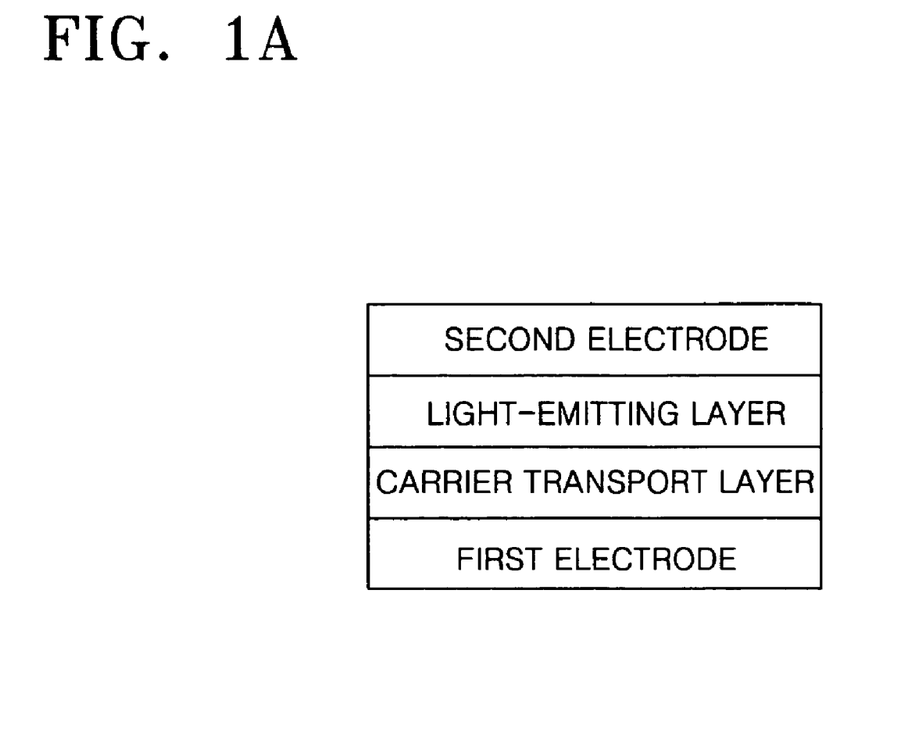
FIGS. 1A and 1B are schematic sectional views illustrating organic light-emitting devices according to embodiments of the present invention.
Figure 1B:
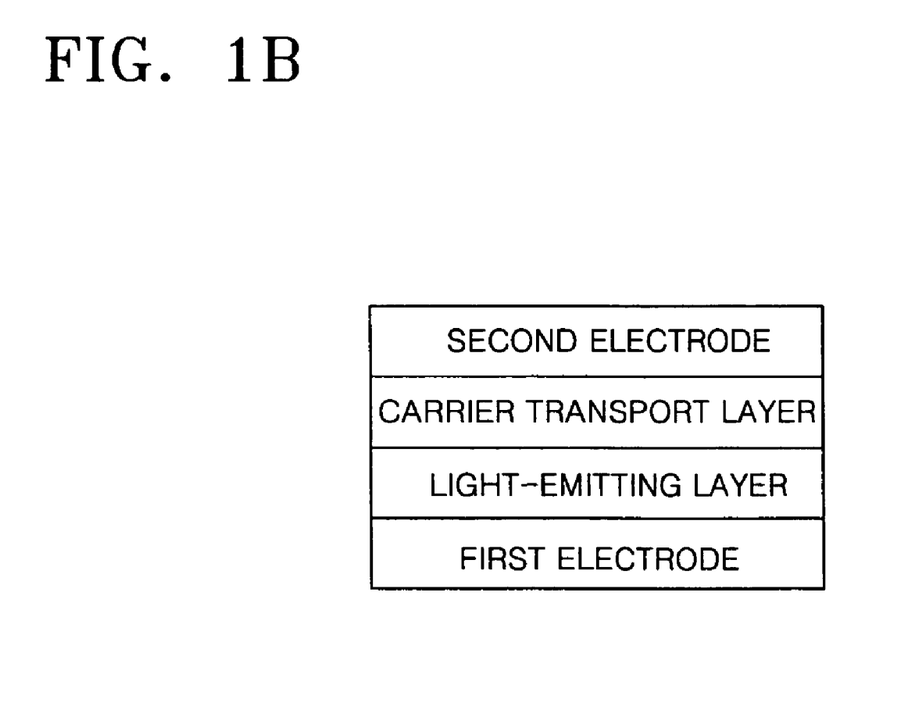

Embodiments of the organic light-emitting device of an embodiment of the present invention are illustrated in FIGS. 1A and 1B. Referring to FIG. 1A, an organic light-emitting device has a stacked structure of a first electrode, a carrier transport layer, a light-emitting layer, and a second electrode. Referring to FIG. 1B, an organic light-emitting device has a stacked structure of a first electrode, a light-emitting layer, a carrier transport layer, and a second electrode. The organic light-emitting device of an embodiment of the present invention is not limited to the structures illustrated in FIGS. 1A and 1B. At least one layer of a hole injection layer, a hole transport layer, an electron blocking layer, a hole blocking layer, an electron transport layer, and an electron injection layer may be further interposed between the first electrode and the second electrode.

Hereinafter, a method of manufacturing an embodiment of the organic light-emitting device of an embodiment of the present invention will be described.

First, a first electrode material with a high work function is formed on a substrate using deposition or sputtering to form a first electrode. The first electrode may be an anode. Here, the substrate may be a substrate commonly used in organic light-emitting devices. Preferably, the substrate may be a glass substrate or a transparent plastic substrate which is excellent in mechanical strength, thermal stability, transparency, surface smoothness, handling property, and water repellency. The first electrode material may be a material with good transparency and conductivity, e.g., indium tin oxide (ITO), indium zinc oxide (IZO), tin oxide ($SnO_2$), or zinc oxide (ZnO).

Next, a hole injection layer (HIL) may be formed on the first electrode using various methods such as vacuum deposition, spin-coating, casting, or Langmuir-Blodgett (LB) method.

In the case of forming the hole injection layer using a vacuum deposition process, the deposition conditions vary according to the type of a hole injection layer material, the structure and thermal characteristics of the hole injection layer, etc. However, it is preferred that the hole injection layer is deposited to a thickness of 10 Å to 5 μm at a temperature of 100 to 500° C., in a vacuum level of $10^{-8}$ to $10^{-3}$ torr, at a deposition rate of 0.01 to 100 Å/sec.

In the case of forming the hole injection layer using a spin-coating process, the coating conditions vary according to the type of a hole injection layer material, the structure and thermal characteristics of the hole injection layer, etc. However, it is preferred that the spin-coating is performed at a coating speed of about 2000 to 5000 rpm, and, after the spin-coating, a thermal treatment is performed at a temperature of about 80 to 200° C. for the purpose of solvent removal.

The hole injection layer material is not particularly limited. For example, the hole injection layer material may be a phthalocyanine compound (e.g., copper phthalocyanine) disclosed in U.S. Pat. No. 4,356,429 which is incorporated herein by reference, a Starburst-type amine derivative (e.g., TCTA, m-MTDATA, or m-MTDAPB) disclosed in *Advanced Material*, 6, p. 677 (1994) which is incorporated herein by reference, or a water-soluble conductive polymer, e.g., Pani/DBSA (Polyaniline/Dodecylbenzenesulfonic acid), PEDOT/PSS (Poly(3,4-ethylenedioxythiophene)/Poly(4- styrenesulfonate)), Pani/CSA (Polyaniline/Camphor sulfonic acid), or PANI/PSS (Polyaniline)/Poly(4-styrene-sulfonate).

Pani/DBSA

PEDOT/PSS

The hole injection layer may be formed to a thickness of about 100 to 10,000 Å, preferably 100 to 1,000 Å. If the thickness of the hole injection layer is less than 100 Å, hole injection characteristics may be lowered. On the other hand, if the thickness of the hole injection layer exceeds 10,000 Å, a driving voltage may be increased.

Next, a hole transport layer (HTL) may be formed on the hole injection layer using various methods such as vacuum deposition, spin-coating, casting, or LB method. In the case of forming the hole transport layer using vacuum deposition or spin-coating, the deposition conditions and the coating conditions vary according to the type of a used compound, but are generally almost the same as those for the formation of the hole injection layer.

A hole transport layer material can be optionally selected from known hole transport layer materials. For example, the hole transport layer material may be a carbazole derivative such as N-phenylcarbazole or polyvinylcarbazole; an amine derivative having a fused ring system such as N,N'-bis(3-methylphenyl)-N,N'-diphenyl-[1,1-biphenyl]-4,4'-diamine (TPD), or N,N'-di(naphthalene-1-yl)-N,N'-diphenylbenzidine (α-NPD); etc.

The hole transport layer may be formed to a thickness of about 50 to 1,000 Å, preferably 100 to 600 Å. If the thickness of the hole transport layer is less than 50 Å, hole transport characteristics may be lowered. On the other hand, if the thickness of the hole transport layer exceeds 1,000 Å, a driving voltage may be increased.

Next, a light-emitting layer (EML) is formed on the hole transport layer using vacuum deposition, spin-coating, casting, or LB method. In the case of forming the light-emitting layer using vacuum deposition or spin-coating, the deposition conditions and the coating conditions vary according to the type of a used compound, but are generally almost the same as those for the formation of the hole injection layer.

A light-emitting layer material is not particularly limited and may be optionally selected from known light-emitting materials. For example, $Alq_3$, CBP (4,4'-N,N'-dicarbazole-biphenyl), PVK (poly(n-vinylcarbazole)), etc. may be used as a host material.

PVK

The light-emitting layer material may include a fluorescent dopant such as IDE102 and IDE105 (commercially available from Idemitsu), or C545T (commercially available from Hayashibara) or a phosphorescent dopant such as a red phosphorescent dopant (e.g., PtOEP, RD 61 (UDC)), a green phosphorescent dopant (e.g., $Ir(PPy)_3$(PPy=2-phenylpyridine), Green K2 (Dow Chemical)), or a blue phosphorescent dopant (e.g., F2Irpic).

The doping concentration of a dopant is not particularly limited. Generally, the content of a dopant is 0.01 to 15 parts by weight based on 100 parts by weight of a host.

The light-emitting layer may be formed to a thickness of about 100 to 1,000 Å, preferably 200 to 800 Å. If the thickness of the light-emitting layer is less than 100 Å, emission characteristics may be lowered. On the other hand, if the thickness of the light-emitting layer exceeds 1,000 Å, a driving voltage may be increased.

In a case where the light-emitting layer includes a phosphorescent dopant, a hole blocking layer (HBL) may be formed on the hole transport layer using vacuum deposition, spin-coating, casting, or LB method, in order to prevent the diffusion of triplet excitons or holes into an electron transport layer. In the case of forming the hole blocking layer using vacuum deposition or spin coating, the deposition conditions and the coating conditions vary according to the type of a used compound, but are generally almost the same as those for the formation of the hole injection layer. An available hole blocking material may be an oxadiazole derivative, a triazole derivative, a phenanthroline derivative, a hole blocking material disclosed in JP 11-329734(A1) which is incorporated herein by reference, bathocuproine (BCP), etc.

The hole blocking layer may be formed to a thickness of about 50 to 1,000 Å, preferably 100 to 300 Å. If the thickness of the hole blocking layer is less than 50 Å, hole blocking characteristics may be lowered. On the other hand, if the thickness of the hole blocking layer exceeds 1,000 Å, a driving voltage may be increased.

Next, an electron transport layer (ETL) may be formed on the light-emitting layer using various methods such as vacuum deposition, spin-coating, or casting. In the case of forming the electron transport layer using vacuum deposition or spin-coating, the deposition conditions and the coating conditions vary according to the type of a used compound, but are generally almost the same as those for the formation of the hole injection layer.

An electron transport layer material may be optionally selected from known electron transport layer materials. The electron transport layer material serves to stably transport electrons from an electron donor electrode (a cathode) to the light-emitting layer, and may be a known material such as a quinoline derivative (in particular, tris(8-quinolinolate)aluminum ($Alq_3$)) or TAZ.

TAZ

The electron transport layer may be formed to a thickness of about 100 to 1,000 Å, preferably 200 to 500 Å. If the thickness of the electron transport layer is less than 100 Å, electron transport characteristics may be lowered. On the other hand, if the thickness of the electron transport layer exceeds 1,000 Å, a driving voltage may be increased.

An electron injection layer (EIL) may be formed on the electron transport layer in order to facilitate the injection of electrons from a cathode into the light-emitting layer. An electron injection layer material is not particularly limited.

The electron injection layer material may be optionally selected from known materials such as LiF, NaCl, CsF, $Li_2O$, or BaO. The deposition conditions of the electron injection layer vary according to the type of a used compound, but are generally almost the same as those for the formation of the hole injection layer.

The electron injection layer may be formed to a thickness of about 1 to 100 Å, preferably 5 to 50 Å. If the thickness of the electron injection layer is less than 1 Å, electron injection characteristics may be lowered. On the other hand, if the thickness of the electron injection layer exceeds 100 Å, a driving voltage may be increased.

Finally, a second electrode is formed on the electron injection layer using vacuum deposition or sputtering. The second electrode may be used as a cathode. A material for forming the second electrode may be metal or alloy with a low work function, an electroconductive compound, or a mixture thereof. For example, the second electrode forming material may be lithium (Li), magnesium (Mg), aluminum (Al), aluminum-lithium (Al—Li), calcium (Ca), magnesium-indium (Mg—In), magnesium-silver (Mg—Ag), etc. The second electrode may also be a transmissive cathode made of ITO or IZO to provide a front-emission type device.

The method of manufacturing the organic light-emitting device according to an embodiment of the present invention may further include forming a carrier transport layer including a silsesquioxane-based compound as described above between any two layers selected from the above-described layers (i.e., a first electrode, a hole injection layer, a hole transport layer, an electron blocking layer, a light-emitting layer, a hole blocking layer, an electron transport layer, an electron injection layer, and a second electrode).

For example, an organic light-emitting device as illustrated in FIG. 1A can be manufactured by forming a first electrode, forming a carrier transport layer including a silsesquioxane-based compound according to an embodiment of the present invention on the first electrode, and sequentially forming a light-emitting layer and a second electrode on the carrier transport layer.

The carrier transport layer can be formed using a known coating or printing process. For example, spin coating, casting, inkjet printing, or contact printing can be used, but the present invention is not limited thereto. In order to facilitate a cross-linkage during forming the carrier transport layer, a thermal treatment may be performed after coating or printing. At this time, the thermal treatment may be performed at a temperature of 30 to 250° C., preferably 80 to 150° C. If the thermal treatment temperature is less than 30° C., a sufficient cross-linking may not occur. On the other hand, if the thermal treatment temperature exceeds 250° C., the silsesquioxane-based compound may be thermally decomposed.

The carrier transport layer may be formed to a thickness of 1 to 150 nm, preferably 5 to 100 nm. If the thickness of the carrier transport layer is less than 1 nm, carrier (i.e., electron or hole) injection characteristics may be lowered. On the other hand, if the thickness of the carrier transport layer exceeds 150 nm, a driving voltage may be increased.

Hereinafter, the present invention will be described more specifically with reference to the following examples, i.e., the synthesis example of a silsesquioxane-based compound according to the present invention, manufacturing examples of organic light-emitting devices, and evaluation example. The following examples are for illustrative purposes and are not intended to limit the scope of the invention.

EXAMPLES

Synthesis Example

Synthesis of Intermediate B

An intermediate B was synthesized according to Reaction Scheme 1 below:

<Reaction Scheme 1> intermediate A

-continued intermediate B

Octavinylsilsesquioxane (POSS, 1 g, 1.57 mmol) and 0.164 g of a complex A, platinum(0)-1,3-divinyl-1,1,3,3-tetramethyldisiloxane complex (solution in xylene) were added to a flask, and the reaction solution was diluted with 300 ml of diethylether. Then, the flask was cooled to −78° C., and 6 equivalents of an intermediate A was gradually added thereto. The reaction solution was gradually heated to room temperature and incubated at room temperature for 20 hours, and a volatile material was removed under a reduced pressure of 0.1 Torr. 100 ml of pentane was added to the resultant solution, and the resultant solution was stirred for one hour and filtered through celite to give a solution. Pentane was removed from the solution under a reduced pressure of 0.1 Torr to yield an intermediate B.

Synthesis of Compound Represented by Formula 7 (Hereinafter, Referred to as "Compound 7")

compound 7

The intermediate B and 0.164 g of a complex A, platinum (0)-1,3-divinyl-1,1,3,3-tetramethyldisiloxane complex (solution in xylene) were added to a flask, and the reaction solution was diluted with 300 ml of diethylether. Then, the flask was cooled to −78° C. and 2 equivalents of trichlorosilane (SiHCl$_3$) was gradually added thereto. The reaction solution was gradually heated to room temperature and incubated at room temperature for 20 hours, and a volatile material was removed under a reduced pressure of 0.1 Torr. 100 ml of pentane was added to the resultant solution, and the resultant solution was stirred for one hour and filtered through celite to give a solution. Pentane was removed from the solution under a reduced pressure of 0.1 Torr to give a compound. The compound was dissolved in 100 ml of THF, followed by addition of triethylamine and gradual addition of 10 equivalents of ethanol. The reaction solution was incubated at room temperature for 10 hours and filtered through celite to give a solution. A solvent was removed from the solution under a reduced pressure of 0.1 Torr to yield a compound 7.

$^1$H-NMR (300 MHz, CDCl$_3$) d (ppm) 0.1(Si—(CH$_3$)$_2$), 0.4(POSS-CH$_2$CH$_2$Si), 0.54(POSS-CH$_2$CH$_2$Si), 1.06(Si—OCH$_2$CH$_3$), 3.67(Si—OCH$_2$CH$_3$), 6.8-7.08(N-Phenyl)

Example

Organic light-emitting devices in which carrier transport layers including the compound 7 were interposed between first electrodes and light-emitting layers were manufactured: IZO/compound 7 (15 nm)/light-emitting layer (70 nm)/Ba(5 nm)/Al(150 nm).

A 15 Ω/cm$^2$ (1,200 Å) IZO glass substrate (Corning) was cut into pieces of 50 mm×50 mm×0.7 mm in size, followed by ultrasonic cleaning in isopropyl alcohol and deionized water (5 minutes for each) and then UV/ozone cleaning (30 minutes) to form anodes. The compound of Formula 7 was coated on the anodes and thermally treated at 120° C. for 5 hours to form carrier transport layers with a thickness of 15 nm. Then, green light-emitting materials (Lumation 1300, K2, Dow Chemical) were spin-coated on the carrier transport layers and thermally treated at 110° C. for 2 hours to form light-emitting layers with a thickness of 70 nm. Then, Ba (5 nm) and Al (150 nm) were sequentially vacuum-deposited on the light-emitting layers to thereby complete organic light-emitting devices as shown in FIG. 1A. The organic light-emitting devices were designated as "samples 1".

Comparative Example

Organic light-emitting devices were manufactured in the same manner as in Example except that no carrier transport layer including the compound 7 was formed on IZO. The organic light-emitting devices were designated as "samples A".

Evaluation Example

Figure 2:
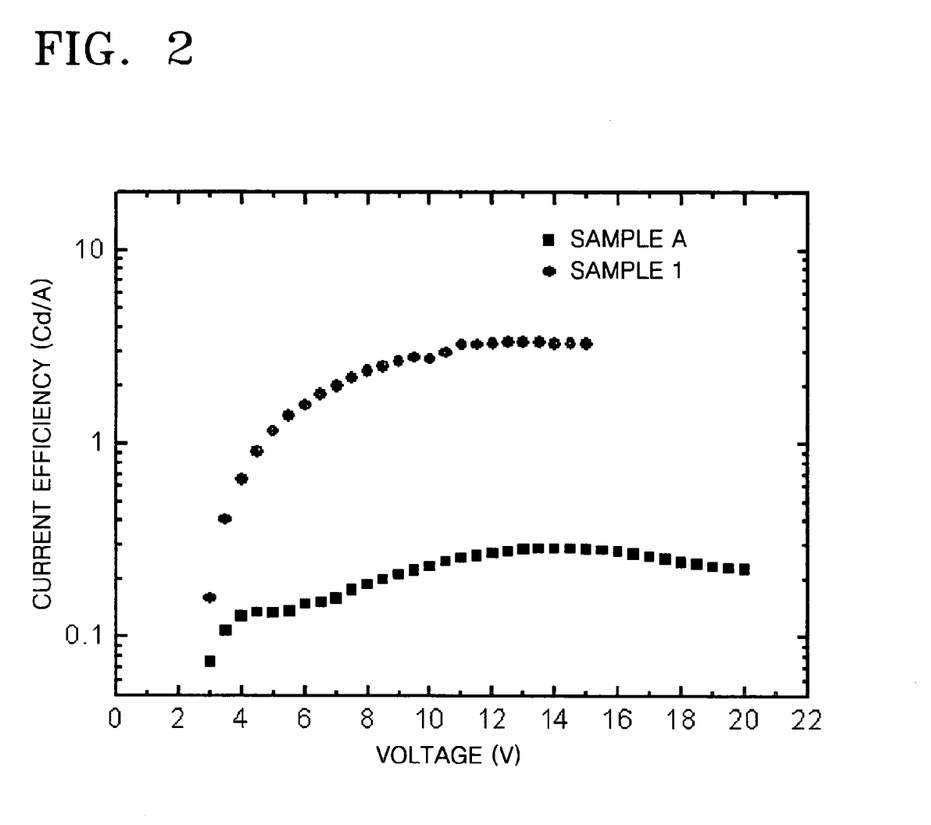
FIG. 2 is a graph illustrating voltage-current efficiency characteristics of an organic light-emitting device according to an embodiment of the present invention and a conventional organic light-emitting device.
Figure 3:
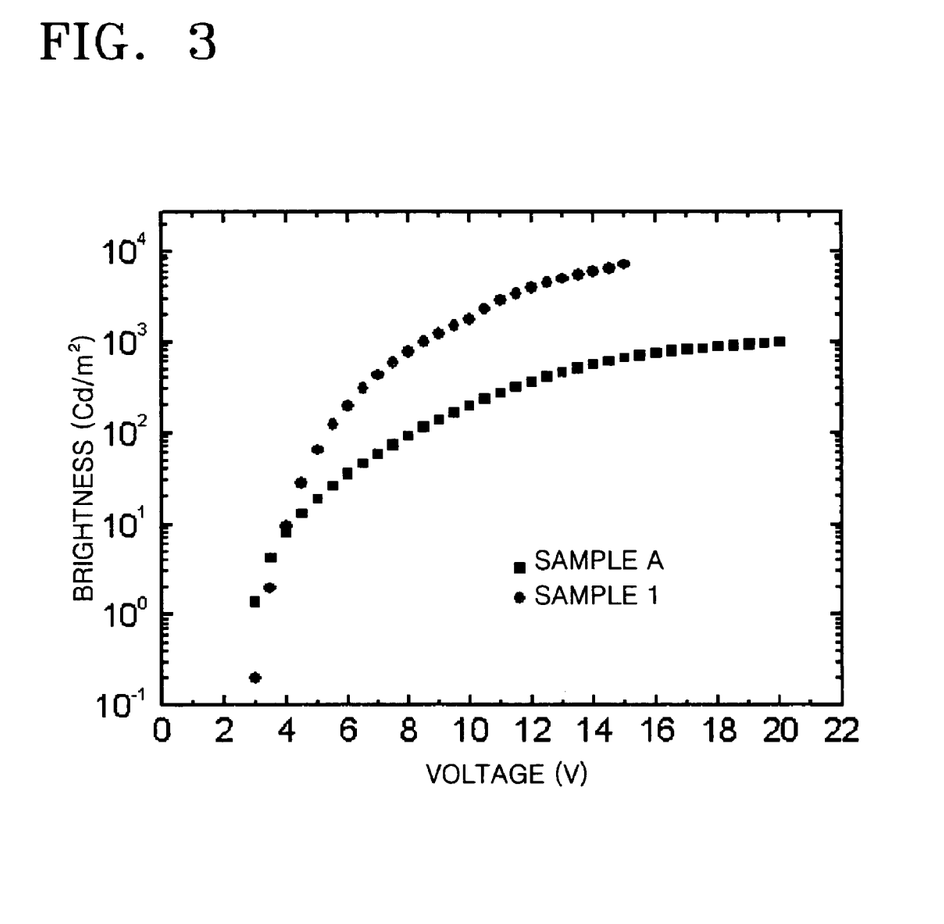
FIG. 3 is a graph illustrating voltage-brightness characteristics of an organic light-emitting device according to an embodiment of the present invention and a conventional organic light-emitting device.

The current efficiency and brightness of the samples 1 and A were evaluated using a PR650 (Spectroscan) Source Measurement Unit, and the results are shown in FIGS. 2 and 3. Referring to FIGS. 2 and 3, the samples 1 (the organic light-emitting devices of embodiments of the present invention) exhibited better current efficiency and brightness than the samples A (the conventional organic light-emitting devices).

A silsesquioxane-based compound according to the present invention can exhibit good film smoothness and adhesion, and at the same time, good electrical characteristics such as current efficiency and brightness, and thus, is suitable for use in an organic light-emitting device.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims

What is claimed is:

1. A silsesquioxane-based compound represented by Formula 1:

(1)

wherein R$_1$, R$_2$, R$_3$, R$_4$, R$_5$, R$_6$, R$_7$, and R$_8$ are each independently a substituent having a hole transport moiety, a substituent having an electron transport moiety, or a substituent having a cross-linkable moiety represented by —Si(M$_1$)(M$_2$)(M$_3$) where M$_1$, M$_2$, and M$_3$ are each independently hydrogen, a C$_1$-C$_{20}$ alkyl group, a C$_1$-C$_{20}$ alkoxy group, or a halogen group, and at least one of M$_1$, M$_2$, and M$_3$ is a C$_1$-C$_{20}$ alkoxy group or a halogen group, and at least one of R$_1$, R$_2$, R$_3$, R$_4$, R$_5$, R$_6$, R$_7$, and R$_8$ is the substituent having the cross-linkable moiety; and wherein at least one of R$_1$, R$_2$, R$_3$, R$_4$, R$_5$, R$_6$, R$_7$, and R$_8$ is one of the following substituents(i)-(iv):

(i) the substituent having the hole transport moiety selected from the group consisting of where Q$_1$, Q$_2$, Q$_3$, Q$_4$, and Q$_5$ are each independently N, O, or S;

(ii) the substituent having the hole transport moiety represented by Formula 3:

(3)

(iii) the substituent having the electron transport moiety selected from the group consisting of where Q$_6$, Q$_7$, and Q$_8$ are each independently N, O, or S; and (iv) the substituent having the electron transport moiety represented by Formula 4:

(4)

2. The silsesquioxane-based compound of claim 1, wherein R$_1$, R$_2$, R$_3$, R$_4$, R$_5$, R$_6$, R$_7$, and R$_8$ are each independently the substituent having the hole transport moiety or the substituent having the cross-linkable moiety, and at least one of R$_1$, R$_2$, R$_3$, R$_4$, R$_5$, R$_6$, R$_7$, and R$_8$ is the substituent having the cross-linkable moiety.

3. The silsesquioxane-based compound of claim 1, wherein R$_1$, R$_2$, R$_3$, R$_4$, R$_5$, R$_6$, R$_7$, and R$_8$ are each independently the substituent having the electron transport moiety or the substituent having the cross-linkable moiety, and at least one of R$_1$, R$_2$, R$_3$, R$_4$, R$_5$, R$_6$, R$_7$, and R$_8$ is the substituent having the cross-linkable moiety.

4. The silsesquioxane-based compound of claim 1, wherein at least one of R$_1$, R$_2$, R$_3$, R$_4$, R$_5$, R$_6$, R$_7$, and R$_8$ is the substituent having the hole transport moiety selected from the group consisting of -continued where $Q_6$, $Q_7$, and $Q_8$ are each independently N, O, or S.

8. The silsesquioxane-based compound of claim 7, wherein at least one atom of the electron transport moiety is substituted by at least one selected from the group consisting of a hydroxyl group, an amino group, a halogen atom, a cyano group, a $C_1$-$C_{20}$ alkyl group, and a $C_1$-$C_{20}$ alkoxy group.

$Q_1$, $Q_2$, $Q_3$, $Q_4$, and $Q_5$ are each independently N, O, or S.

9. The silsesquioxane-based compound of claim 1, wherein at least one of $R_1$, $R_2$, $R_3$, $R_4$, $R_5$, $R_6$, $R_7$, and $R_8$ is the substituent having the electron transport moiety represented by Formula 4:

5. The silsesquioxane-based compound of claim 4, wherein at least one atom of the hole transport moiety is substituted by at least one selected from the group consisting of a hydroxyl group, an amino group, a halogen atom, a cyano group, a $C_1$-$C_{20}$ alkyl group, and a $C_1$-$C_{20}$ alkoxy group.

6. The silsesquioxane-based compound of claim 1, wherein at least one of $R_1$, $R_2$, $R_3$, $R_4$, $R_5$, $R_6$, $R_7$, and $R_8$ is the substituent having the hole transport moiety represented by Formula 3:

(3)

(4)

10. The silsesquioxane-based compound of claim 1, wherein the substituent having the cross-linkable moiety is represented by Formula 5:

7. The silsesquioxane-based compound of claim 1, wherein at least one of $R_1$, $R_2$, $R_3$, $R_4$, $R_5$, $R_6$, $R_7$, and $R_8$ is the substituent having the electron transport moiety selected from the group consisting of (5)

11. The silsesquioxane-based compound of claim 1, which is represented by one of Formulae 6 and 7:

(6)

(7)

-continued

12. An organic light-emitting device comprising:
a first electrode;
a second electrode;
a light-emitting layer interposed between the first electrode and the second electrode; and
a carrier transport layer interposed between the first electrode and the second electrode, the carrier transport layer comprising the silsesquioxane-based compound of claim 1.

13. An organic light-emitting device comprising:
a first electrode;
a second electrode;
a light-emitting layer interposed between the first electrode and the second electrode; and
a carrier transport layer interposed between the first electrode and the second electrode, the carrier transport layer comprising a silsesquioxane-based compound represented by Formula 2:

(2)

wherein a, b, c, d, e, f, g, and h are each independently an integer of 1 to 20;
$T_1$, $T_2$, $T_3$, $T_4$, $T_5$, $T_6$, $T_7$, and $T_8$ are each independently C or Si;
$X_1$, $X_2$, $X_3$, $X_4$, $X_5$, $X_6$, $X_7$, $X_8$, $Y_1$, $Y_2$, $Y_3$, $Y_4$, $Y_5$, $Y_6$, $Y_7$, and $Y_8$ are each independently hydrogen or a $C_1$-$C_{20}$ alkyl group; and
$Z_1$, $Z_2$, $Z_3$, $Z_4$, $Z_5$, $Z_6$, $Z_7$, and $Z_8$ are each independently a hole transport moiety, an electron transport moiety, or a cross-linkable moiety represented by —Si($M_1$)($M_2$)($M_3$) where $M_1$, $M_2$, and $M_3$ are each independently hydrogen, a $C_1$-$C_{20}$ alkyl group, a $C_1$-$C_{20}$ alkoxy group, or a halogen group, and at least one of $M_1$, $M_2$, and $M_3$ is a $C_1$-$C_{20}$ alkoxy group or a halogen group, and at least one of $Z_1$, $Z_2$, $Z_3$, $Z_4$, $Z_5$, $Z_6$, $Z_7$, and $Z_8$ is the cross-linkable moiety.

14. The organic light-emitting device of claim 13, wherein the hole transport moiety is selected from the group consisting of -continued -continued where $Q_1, Q_2, Q_3, Q_4,$ and $Q_5$ are each independently N, O, or S;

the electron transport moiety is selected from the group consisting of $Q_6, Q_7,$ and $Q_8$ are each independently N, O, or S; and the cross-linkable moiety is represented by $—Si(M_1)(M_2)(M_3)$ where $M_1, M_2,$ and $M_3$ are each independently hydrogen, a $C_1$-$C_{20}$ alkyl group, a $C_1$-$C_{20}$ alkoxy group, or a halogen group, and at least one of $M_1, M_2,$ and $M_3$ is a $C_1$-$C_{20}$ alkoxy group or a halogen group.

15. An organic light-emitting device comprising:
a first electrode;
a second electrode;
a light-emitting layer interposed between the first electrode and the second electrode; and
a carrier transport layer interposed at least one of between the first electrode and the light-emitting layer and between the light-emitting layer and the second electrode, the carrier transport layer comprising the silsesquioxane-based compound represented by Formula 1:

<Formula 1> wherein $R_1, R_2, R_3, R_4, R_5, R_6, R_7,$ and $R_8$ are each independently a substituent having a hole transport moiety, a substituent having an electron transport moiety, or a substituent having a cross-linkable moiety represented by $—Si(M_1)(M_2)(M_3)$ where $M_1, M_2,$ and $M_3$ are each independently hydrogen, a $C_1$-$C_{20}$ alkyl group, a $C_1$-$C_{20}$ alkoxy group, or a halogen group, and at least one of $M_1, M_2,$ and $M_3$ is a $C_1$-$C_{20}$ alkoxy group or a halogen group, and at least one of $R_1, R_2, R_3, R_4, R_5, R_6, R_7,$ and $R_8$ is the substituent having the cross-linkable moiety.

16. The organic light-emitting device of claim 15, wherein the carrier transport layer further comprises metal nanoparticles.

17. The organic light-emitting device of claim 16, wherein the metal nanoparticles are at least one selected from the group consisting of Au, Ag, Cu, Pd, and Pt nanoparticles.

18. The organic light-emitting device of claim 16, wherein the metal nanoparticles have an average particle size of 5 to 20 nm.

19. The organic light-emitting device of claim 15, further comprising at least one layer selected from the group consisting of a hole injection layer, a hole transport layer, an electron blocking layer, a hole blocking layer, an electron transport layer, and an electron injection layer, said at least one layer interposed between the first electrode and the second electrode.

* * * * *